(12) United States Patent
Nho et al.

(10) Patent No.: US 11,285,186 B2
(45) Date of Patent: Mar. 29, 2022

(54) **COMPOSITION COMPRISING *CREPIDIASTRUM DENTICULATUM* EXTRACT FOR PREVENTING OR TREATING ISCHEMIA-REPERFUSION INJURY AND USE THEREOF**

(71) Applicants: KOREA INSTITUTE OF SCIENCE AND TECHNOLOGY, Seoul (KR); UNIVERSITY OF ULSAN FOUNDATION FOR INDUSTRY COOPERATION, Ulsan (KR)

(72) Inventors: Chu Won Nho, Seoul (KR); Hak Cheol Kwon, Seoul (KR); Ji-Hye Yoo, Seoul (KR); Jaeyoung Kwon, Seoul (KR); Jin Soo Park, Seoul (KR); Hyuk-Jai Jang, Seoul (KR); Seong-Su Kim, Seoul (KR); Cheon Soo Park, Seoul (KR); Hwa-Mi Lee, Seoul (KR); Hee Ju Lee, Seoul (KR)

(73) Assignees: KOREA INSTITUTE OF SCIENCE AND TECHNOLOGY, Seoul (KR); UNIVERSITY OF ULSAN FOUNDATION FOR INDUSTRY COOPERATION, Ulsan (KR)

(*) Notice: Subject to any disclaimer, the term of this patent is extended or adjusted under 35 U.S.C. 154(b) by 225 days.

(21) Appl. No.: 16/555,950

(22) Filed: Aug. 29, 2019

(65) Prior Publication Data
US 2019/0381122 A1 Dec. 19, 2019

Related U.S. Application Data

(62) Division of application No. 15/717,337, filed on Sep. 27, 2017, now abandoned.

(51) Int. Cl.
| | |
|---|---|
| *A61K 36/28* | (2006.01) |
| *A61P 9/10* | (2006.01) |
| *A23L 33/00* | (2016.01) |
| *A23L 33/105* | (2016.01) |

(52) U.S. Cl.
CPC ............ *A61K 36/28* (2013.01); *A23L 33/105* (2016.08); *A23L 33/30* (2016.08); *A23L 33/40* (2016.08); *A61P 9/10* (2018.01); *A23V 2002/00* (2013.01)

(58) Field of Classification Search
None
See application file for complete search history.

(56) References Cited

U.S. PATENT DOCUMENTS

2005/0244514 A1  11/2005  Zhang

FOREIGN PATENT DOCUMENTS

| KR | 10-2005-0003378 A | 1/2005 |
| KR | 10-2005-0007955 A | 1/2005 |
| KR | 10-2011-0139582 A | 12/2011 |
| KR | 10-140036 | 5/2014 |
| KR | 10-2016-0023310 A | 3/2016 |
| WO | WO 03/090767 A1 | 11/2003 |

OTHER PUBLICATIONS

Ahn et al., "Hydroxycinnamic Acids in Crepidiastrum denticulatum Protect Oxidative Stress-Induced Retinal Damage," Journal of Agricultural and Food Chemistry, vol. 62 (2014) pp. 1310-1323.

Jang et al., "protective effect of crepidiastrum denticulatum extract pretreatment against hepatic ischemia-reperfusion injury in mice," published on Aug. 20, 2016 as a Poster at 26th International Congress of the Transplantation Society (TTS 2016).

Jang et al., "Protective Effect of Crepidiastrum Denticulatum Extract Pretreatment Against Hepatic Ischemia-Reperfusion Injury in Mice," published on May 20, 2016 as a Poster at 2016-year Korean Society for Transplantation 12th Spring Symposium.

Kang et al., "Youngia denticulata Protects Against Oxidative Damage Induced by tert-Butylhydroperoxide in HepG2 Cells," Journal of Medicinal Food, vol. 14(10) 2011, pp. 1198-1207.

Notice of Allowance issued in Korean Patent Application 10-2016-0125103, dated Aug. 29, 2017.

*Primary Examiner* — Susan Hoffman
(74) *Attorney, Agent, or Firm* — Birch, Stewart, Kolasch & Birch, LLP

(57) ABSTRACT

Provided are a pharmaceutical composition including a *Crepidiastrum denticulatum* extract as an active ingredient; and a method for preventing or treating ischemia-reperfusion injury in a subject by using a food composition or the pharmaceutical composition.

19 Claims, 9 Drawing Sheets

[FIG. 1]
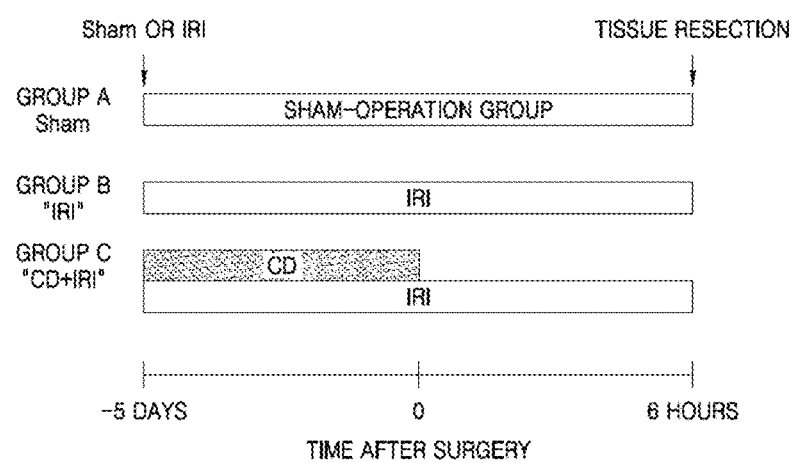

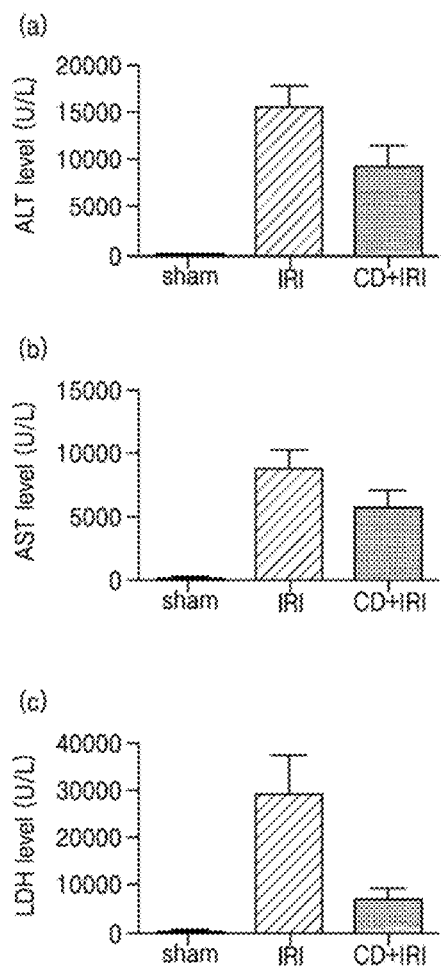
[FIG. 2]

[FIG. 3]
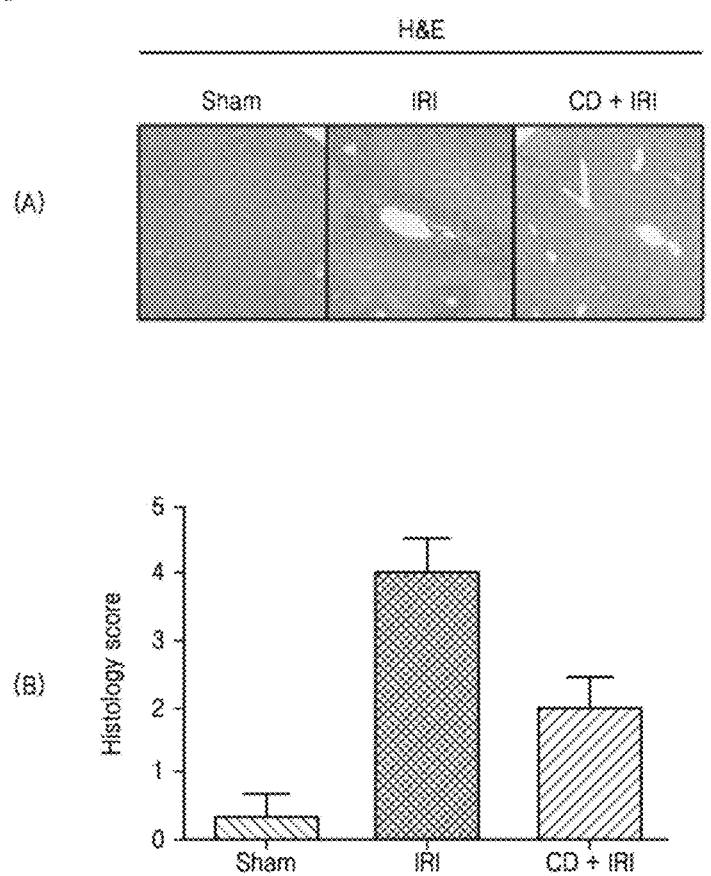

[FIG. 4]
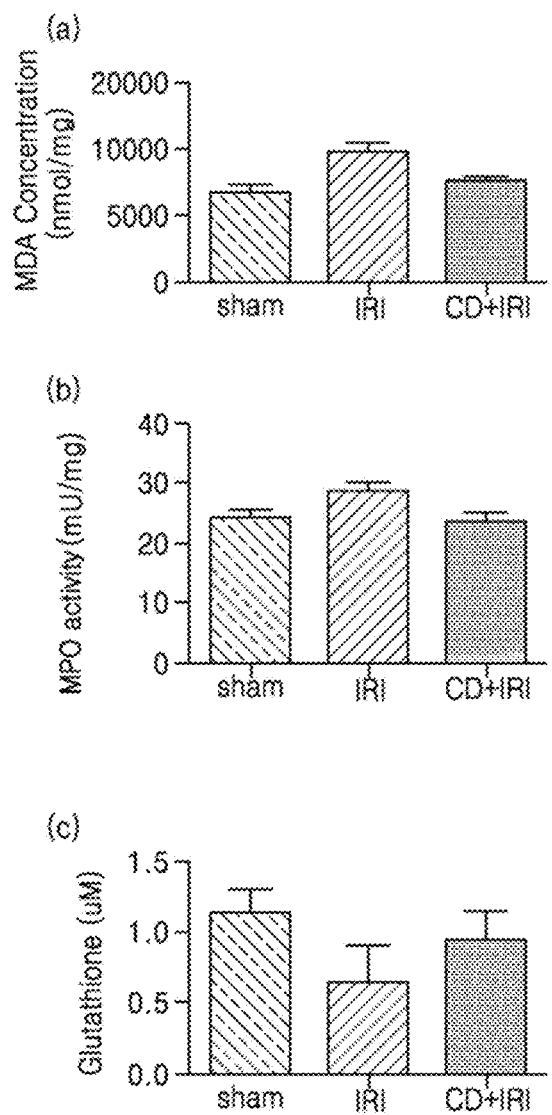

[FIG. 5]
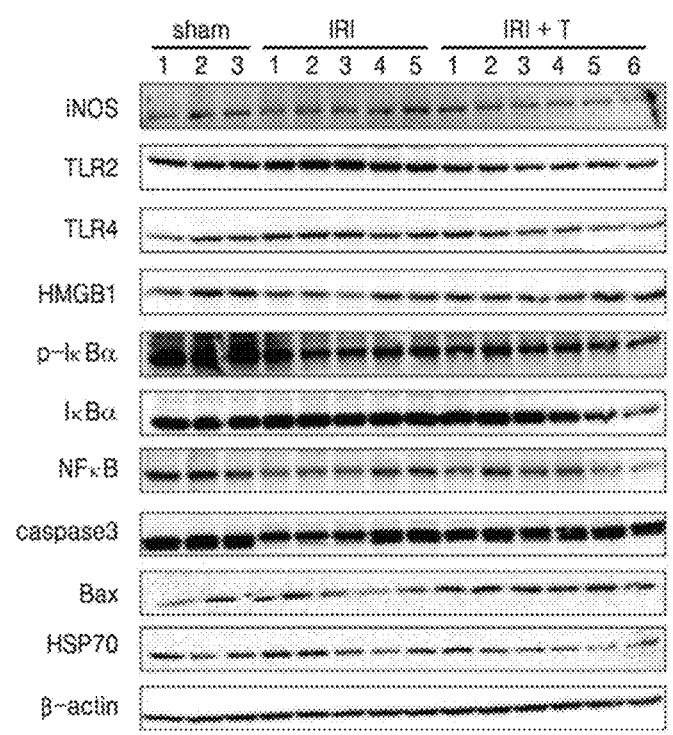

[FIG. 6]
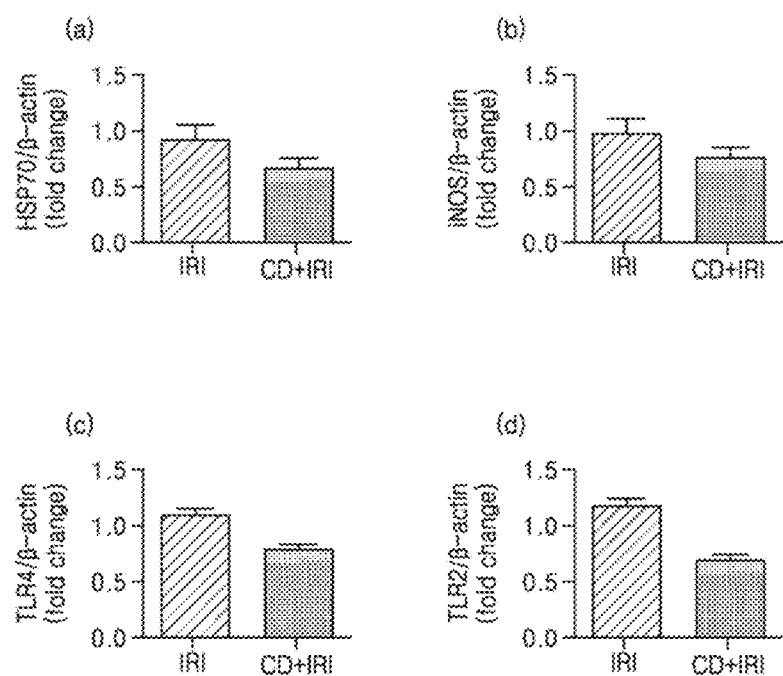

[FIG. 7]
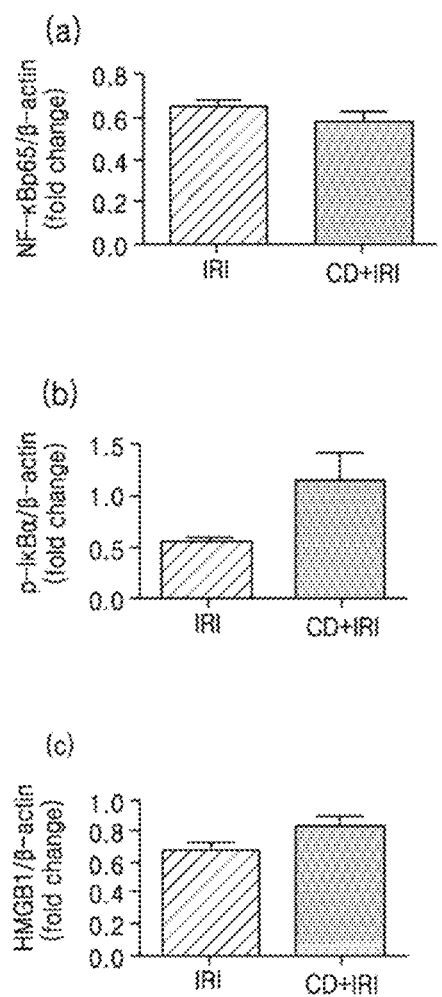

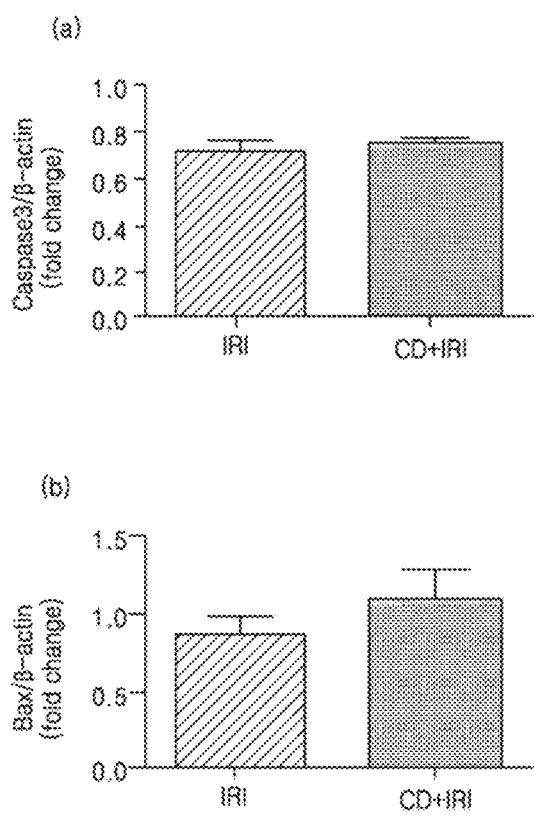
[FIG. 8]

[FIG. 9]
(a)
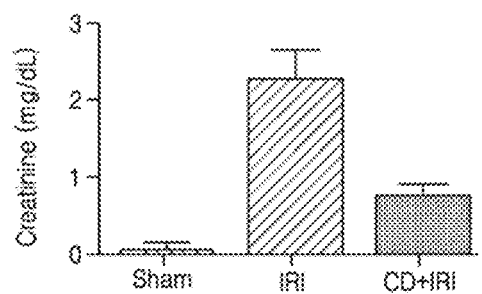
(b)
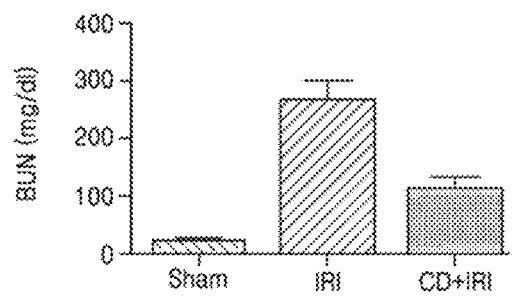

COMPOSITION COMPRISING *CREPIDIASTRUM DENTICULATUM* EXTRACT FOR PREVENTING OR TREATING ISCHEMIA-REPERFUSION INJURY AND USE THEREOF

CROSS-REFERENCE TO RELATED APPLICATION

This application is a Divisional of copending U.S. application Ser. No. 15/717,337, filed on Sep. 27, 2017, now abandoned, which claims the benefit of Korean Patent Application No. 10-2016-0125103, filed on Sep. 28, 2016, in the Korean Intellectual Property Office, the entire contents of all are hereby incorporated by reference.

BACKGROUND

1. Field

One or more embodiments relate to a pharmaceutical composition including a *Crepidiastrum denticulatum* extract as an active ingredient for preventing or treating ischemia-reperfusion injury in a subject, and a method of preventing or treating ischemia-reperfusion injury by using a food composition or the pharmaceutical composition.

2. Description of the Related Art

During surgical procedures such as organ transplantation or surgery for cardiovascular diseases, blood supply to specific tissues may be restricted, and in those cases, continuous blood supply to important organs such as liver, kidney, heart, and brain may be blocked, which may result in damage to the organs induced by ischemia. In addition, when blood flow is suddenly increased by reperfusion in an ischemic state in which oxygen is not supplied properly, cells and tissues may be severely damaged due to various complex causes. Particularly, liver or renal ischemia-reperfusion injury (IRI) is a major complication that occurs frequently after liver or renal transplantation or cardiac surgery. Reperfusion, which is followed by temporary interruption of blood supply to the liver or kidney by intervention of blood flow during surgery, can lead to a severe acute inflammation response and acute tissue injury (J. V. Bonventre et al., Ischemic Kidney Int, 2004, 66, 480-485). In particular, this acute inflammatory reaction or cell apoptosis due to tissue injury is recognized as a very serious risk factor as it is one of the main causes of hepatic failure or renal failure (R. Bonegio et al., Curr Opin Nephrol Hypertension 2002, 11, 301-308). Ischemia-reperfusion injury may be caused by an abrupt increase in intracellular calcium concentration due to sudden increase in blood flow in an oxygen-deficient state. An increase in intracellular calcium may mediate mitochondrial damage, where ATP reacts with a substance released from the mitochondrial damage, which generates active oxygen, and the body may recognize the active oxygen as inflammation, which causes an attack by white blood cells and generates more active oxygen, resulting in cell damage. Ischemia-reperfusion injury is more severe when blood is re-introduced at a higher rate. Ischemia-reperfusion injury occurs frequently when blood flow resumes after cardiac surgery or organ transplant surgery. It has been reported that when such ischemia-reperfusion injury is predicted, damage caused by active oxygen is considered to be one of the main factors causing the damage, and a powerful antioxidant is administered in advance as a therapeutic agent in order to prevent ischemia-reperfusion injury. However, even use of strong antioxidants have been limited due to their limitations, and although clinical studies on some drugs have been conducted, drugs for directly preventing or treating ischemia-reperfusion injury have not been developed to date. Surgical procedures that can cause ischemia-reperfusion injury, such as organ transplantations, are increasing rapidly in the world. However, the development of a new technique that may recover functions of organs while suppressing an inflammatory reaction and cell apoptosis after ischemia-reperfusion injury, which is a problem in liver or kidney transplantation, is urgently needed in medicine and society.

*Crepidiastrum denticulatum* is an annual or biennial plant of Asteraceae. It grows in dry places of mountains or fields and grows to a height of 30 cm to 70 cm, with a thin purple stem. The leaves on the roots are shaped like spatulas and begin to fall when the flowers have bloomed. The leaves on the stem alternate and have no petioles. The leaves may have a length of 6 cm to 11 cm and a width of 3 cm to 7 cm, where ends of the leaves are dull in its shape. The lower part of the leaves is shaped like an ear, which wraps around half of the stem, and sawteeth are sparsely found on their edges. The flower blooms in August to September with a yellow color, and the flower is 15 mm in diameter. The flowers bloom in corymbs which are erect when the flowers bloom and fall down when the flowers fall. The fresh sprout of *Crepidiastrum denticulatum* can be eaten as a boiled vegetable, and it is distributed in Korea, Japan, China, and Indochina.

Korean Patent Publication No. 1020160023310 discloses a cosmetic composition for preventing or delaying skin aging, including *Crepidiastrum denticulatum* extract as an active ingredient. Korean Patent Publication No. 1020110139582 discloses a method of preparing an extract having hangover-relieving effect and an ethanolic liver-detoxifying action by including a *Crepidiastrum denticulatum* extract.

However, even in the prior art, the effect of a *Crepidiastrum denticulatum* extract in preventing or treating tissue damage caused by ischemia-reperfusion injury has not been disclosed so far.

SUMMARY

One or more embodiments include a pharmaceutical composition including an extract of *Crepidiastrum* sp. plant as an active ingredient for preventing or treating ischemia-reperfusion injury in a subject.

One or more embodiments include a food composition including an extract of *Crepidiastrum* sp. plant as an active ingredient for preventing or treating ischemia-reperfusion injury in a subject.

One or more embodiments include a method of preventing or treating ischemia-reperfusion injury in a subject, the method including administering the pharmaceutical composition to the subject.

BRIEF DESCRIPTION OF THE DRAWINGS

These and/or other aspects will become apparent and more readily appreciated from the following description of the embodiments, taken in conjunction with the accompanying drawings in which:

FIG. 1 shows preparation of mouse models and a schedule for drug administration and tissue removal;

FIGS. 2A, 2B, and 2C show alanine aminotransferase (ALT), aspartate aminotransferase (AST), and lactate dehydrogenase (LDH) levels, respectively in serum when a *Crepidiastrum denticulatum* extract-containing composition was administrated to a hepatic ischemia-reperfusion injury (IRI) mouse model;

FIGS. 3A, and 3B show the results of hematoxylin-eosin (H&E) staining of liver tissue when the *Crepidiastrum denticulatum* extract-containing composition was administered to a hepatic IRI mouse model and histology score obtained from H&E staining, respectively;

FIGS. 4A, 4B, and 4C show the results of measuring MDA, MPO, and glutathione levels, respectively in liver tissue when the *Crepidiastrum denticulatum* extract-containing composition was administered to a hepatic IRI mouse model;

FIGS. 5, 6A-6D, 7A-7C, 8A, and 8B show the Western-blot results of main factors acting to produce the effect of the *Crepidiastrum denticulatum* extract-containing composition with respect to IRI; and FIGS. 9A, and 9B show a BUN level in blood and a creatinine level in serum when the *Crepidiastrum denticulatum* extract-containing composition was administrated to a renal IRI mouse model, respectively.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment, provided is a pharmaceutical composition including an extract of *Crepidiastrum* sp. plant as an active ingredient for preventing or treating ischemia-reperfusion injury in a subject.

The *Crepidiastrum* sp. plant may be *Crepidiastrum denticulatum* (Houtt.), *Crepidiastrum sonchifolium* (Bunge), *Crepidiastrum lanceolatum* (Houtt.), *Crepidiastrum chelidoniifolium* (Makino), *Crepidiastrum platyphyllum* (Franch. & Sav.), or *Crepidiastrum koidzumianum*.

The plant may include the whole plant or a part of the plant. The part may refer to a portion on the ground, i.e., aerial part or a portion under the ground. The portion on the ground may refer to a stem, a leaf, a flower, or a combination thereof. The portion under the ground may refer to a root.

The extract may be extracted from the plant by using water, a C1-C6 alcohol, or a mixture thereof as an extracting solvent. The alcohol may be a C1-C3 alcohol, a C1-C4 alcohol, a C1-C5 alcohol, or a C1-C6 alcohol. The alcohol may be a primary alcohol. The C1-C6 alcohol may be methanol, ethanol, propanol, isopropanol, butanol, or a mixture thereof.

The extraction may include immersing the plant in the solvent for a predetermined period of time. The extraction may include a stirring or heating process. The heating process may include heating up to 50° C., 60° C., 70° C., 80° C., or a reflux temperature. The heating process may include heating up to a temperature in a range of about 50° C. to a reflux temperature, about 60° C. to a reflux temperature, about 70° C. to a reflux temperature, about 80° C. to a reflux temperature, or up to a reflux temperature. The extraction time varies depending on the selected temperature, which may be in a range of about 1 hour to about 2 months, for example, about 1 hour to about 1 month, about 1 hour to about 15 days, about 1 hour to about 10 days, about 1 hour to about 5 days, about 1 hour to about 3 days, about 1 hour to about 2 days, about 1 hour to about 1 day, about 5 hours to about 1 month, about 5 hours to about 15 days, about 5 hours to about 10 days, about 5 hours to about 5 days, about 5 hours to about 3 days, about 5 hours to about 2 days, about 5 hours to about 1 day, about 10 hours to about 1 month, about 10 hours to about 15 days, about 10 hours to about 10 days, about 10 hours to about 5 days, about 10 hours to about 3 days, or about 10 hours to about 2 days. The extraction may be reflux extraction of the plant in the solvent. A volume of the solvent may be about 1-fold, 2-fold, 5-fold, 10-fold, or 15-fold or more of a weight of the plant. A volume of the solvent may be in a range of about 1-fold to about 15-fold, for example, about 2-fold to about 15-fold, about 5-fold to about 15-fold, about 10-fold to about 15-fold, or about 15-fold of a weight of the plant. The plant may be dried in shade.

The extraction may include a process of removing the solvent by using a general method such as reduced-pressure concentration of the obtained extract. The extraction may include a process of drying such as freeze-drying the obtained extract to prepare a dried extract.

In particular, the extraction may include a process of obtaining an extract by mixing the whole or the aerial part of a *Crepidiastrum* sp. plant such as *Crepidiastrum denticulatum* with a solvent and incubating the resultant to perform extraction in the solvent; filtering an extract from the solvent; and drying after reduced-pressure concentration of the filtered extract.

Examples of the extraction method may include methods used in the art such as filtration, hot water extraction, immersion extraction, reflux cooling extraction, pressure extraction, subcritical extraction, supercritical extraction, and ultrasonic extraction. For example, the extraction method may be a hot water extraction method. The hot water extraction may include one to five times of extraction. The reduced-pressure concentration may be performed using a vacuum reduced-pressure decompression concentrator or a vacuum rotary evaporator. Further, the drying may be reduced-pressure drying, vacuum drying, boil drying, spray drying, or freeze-drying.

The ischemia may be naturally or artificially generated. Artificially generated ischemia involves artificially reducing blood flow in the blood vessels, which may include clogging or blocking blood vessels. The blocking of a blood vessel includes applying pressure to the blood vessel so that a cross-sectional area of the blood vessel may reduce. The reducing of the cross-sectional area of the blood vessel includes clamping or severing the blood vessel. Also, the artificial reduction of blood flow may be performed during surgery. The surgery may include transplantation, tissue resection, aneurysm repair surgery, or endarterectomy. The tissue transplantation may be heart, liver, kidney, lung, pancreas, stomach, small intestine, or large intestine transplantation. The tissue resection includes liver, kidney, lung, stomach, small intestine, or large intestine resection.

Naturally generated ischemia may be caused by ischemic disorders that generate ischemia. The disorders causing ischemia may include inflammatory diseases, myocardial infarction, atherosclerosis, peripheral vascular disorders, pulmonary embolus, venous thrombosis, transient ischemic attack, unstable angina, cerebral vascular ischemia, stroke, ischemic neurological disorders, ischemic kidney diseases, vasculitis, or traumatic injury. The inflammatory diseases may include rheumatoid arthritis or systemic lupus erythematosus.

The reperfusion may be natural or artificial reperfusion. Artificial reperfusion involves artificially increasing blood flow in the blood vessels. Artificially increasing blood flow involves opening a clogged or occluded vessel or ligating a severed vessel. Artificially increasing blood flow includes supplying blood from the outside of the body. At least one of the ischemia and the reperfusion may be artificially generated.

The ischemia and the reperfusion may be acute. As used herein, the term "acute" refers to a rapid rate of ischemia or reperfusion leading to tissue damage at a rapid rate. Acute ischemia and/or reperfusion may involve vascular occlusion and opening. The blood vessel may be an artery, for example, an aorta, a kidney artery, or a hepatic vein, for example, a portal vein. Acute ischemia and/or reperfusion may involve complete occlusion and opening of blood vessels.

The ischemia-reperfusion injury may be an ischemia-reperfusion injury caused by temporarily blocking the blood flow in the surgical procedure or by temporarily closing and re-opening the blood vessel in the surgical procedure.

The ischemia or reperfusion may last for 3 minutes, 5 minutes, 10 minutes, 15 minutes, 20 minutes, 30 minutes, or 60 minutes or more. The ischemia may last for 3 to 60 minutes, 5 to 60 minutes, 10 to 60 minutes, 15 to 60 minutes, 20 to 60 minutes, 30 to 60 minutes, 3 to 50 minutes, 3 to 30 minutes, 3 to 15 minutes, 5 to 60 minutes, 5 to 30 minutes, 10 to 60 minutes, 10 to 30 minutes, 15 to 60 minutes, or 15 to 30 minutes.

The ischemia-reperfusion injury may be injury to a liver, kidney, heart, lung, small intestine, large intestine, or pancreas.

Particularly, the ischemia-reperfusion injury may be a disease generated by damage caused by any one of the following ischemic diseases: a surgical procedure for temporarily occluding any arterial portion as in renal cancer resection; ex vivo culture, preservation, and re-transplantation procedures for organs requiring transplantation such as kidney, heart, liver, lung, small intestine, or pancreas; blood flow reduction or interruption caused by clamping of blood vessels during a surgical procedure or hemostasis procedure and recovery of oxygen and/or nutrient inflow to the tissue; or other tissue damage leading to hypoxia, ischemia, or severe traumatic anatomical and functional lesions that may lead to death by cell death or malfunction.

The composition may be for administration before, during, or after the occurrence of ischemia-reperfusion injury. The administration may be for administration before, during, or after surgery. The composition may be for administration before, during, or after closure of a blood vessel in advance of surgery. The blood vessel may be an artery, for example, the aorta. The surgery may include performing vascular occlusion and reperfusion alternately, wherein the administration may be administration before the vascular occlusion, between the vascular occlusion and the reperfusion, or during the reperfusion. The composition may be used for an ischemia-reperfusion injury caused by organ transplantation of any one or more of liver, kidney, heart, lung, small intestine, or pancreas or may be acute ischemia-reperfusion injury occurring after the transplantation.

The composition may include the extract at an amount in a range of about 0.001 wt % to about 80 wt %, for example, about 0.01 wt % to about 60 wt %, about 0.01 wt % to about 40 wt %, about 0.01 wt % to about 30 wt %, about 0.01 wt % to about 20 wt %, about 0.01 wt % to about 10 wt %, about 0.01 wt % to about 5 wt %, about 0.05 wt % to about 60 wt %, about 0.05 wt % to about 40 wt %, about 0.05 wt % to about 30 wt %, about 0.05 wt % to about 20 wt %, about 0.05 wt % to about 10 wt %, about 0.05 wt % to about 5 wt %, about 0.1 wt % to about 60 wt %, about 0.1 wt % to about 40 wt %, about 0.1 wt % to about 30 wt %, about 0.1 wt % to about 20 wt %, about 0.1 wt % to about 10 wt %, or about 0.1 wt % to about 5 wt % of the total weight of the composition.

The composition may include a pharmaceutically or nutraceutically acceptable diluent or carrier. The carrier may be an excipient, a disintegrant, a binder, a lubricant, or a combination thereof. The excipient may be microcrystalline cellulose, lactose, low-substituted hydroxy cellulose, or a combination thereof. The disintegrant may be sodium starch glycolate, anhydrous calcium monohydrogen phosphate, or a combination thereof. The binder may be polyvinylpyrrolidone, low-substituted hydroxypropylcellulose, hydroxypropylcellulose, or a combination thereof. The lubricant may be magnesium stearate, silicon dioxide, talc, or a combination thereof.

The composition may be formulated into an oral or parenteral dosage formulation. The parenteral dosage formulation may be an injectable formulation.

The composition may be a pharmaceutical or food composition.

According to another aspect of an embodiment, provided is a food composition for preventing or treating ischemia-reperfusion injury in a subject, the composition including an extract of *Crepidiastrum* sp. plant as an active ingredient. The food may be a functional food.

The food composition may contain various flavors or natural carbohydrates as an additional ingredient. The natural carbohydrates may be monosaccharides such as glucose and fructose, disaccharides such as maltose and sucrose, and polysaccharides such as dextrin and cyclodextrin, and sugar alcohols such as xylitol, sorbitol, and erythritol. Examples of sweeteners include natural sweeteners such as thaumatin and *stevia* extracts; and synthetic sweeteners such as saccharin and aspartame. A content of the natural carbohydrate may be selected from a range of 0.01 to 0.04 parts by weight, for example, about 0.02 to 0.03 parts by weight based on 100 parts by weight of the composition.

In addition to the examples above, the food composition may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohol, and carbonating agents used in carbonated drinks. In addition, the functional food of the present invention may contain flesh for preparation of natural fruit juice, fruit juice drinks, and vegetable drinks.

According to another embodiment, provided is a method of preventing or treating ischemia-reperfusion injury in a subject, the method including administrating the pharmaceutical composition to a subject.

Such administration may be performed by using methods known in the art. Administration may be by direct administration to an individual by any means, for example, by intravenous, intramuscular, oral, or subcutaneous administration. The administration may be systemically or locally administered. The administration may be topical administration to a site where ischemia-reperfusion injury is present or is expected to occur.

The subject may be a mammal, such as a human, a cow, a horse, a pig, a dog, a sheep, a goat, or a cat.

Such administration may be by administering a "therapeutically effective amount" sufficient to prevent or treat ischemia-reperfusion injury in a subject. The administration may include administering the extract at an amount in a range of about 0.1 mg to about 1,000 mg, for example, about 0.1 mg to about 500 mg, about 0.1 mg to about 100 mg, about 0.1 mg to about 50 mg, about 0.1 mg to about 25 mg, about 1 mg to about 1000 mg, about 1 mg to about 500 mg, about 1 mg to about 100 mg, about 1 mg to about 50 mg, about 1 mg to about 25 mg, about 5 mg to about 1,000 mg, about 5 mg to about 500 mg, about 5 mg to about 100 mg, about 5 mg to about 50 mg, about 5 mg to about 25 mg, about 10 mg to about 1,000 mg, about 10 mg to about 500 mg, about 10 mg to about 100 mg, about 10 mg to about 50 mg, or about 10 mg to about 25 mg per a subject.

The administration may be performed before, during, or after the occurrence of ischemia-reperfusion injury.

Hereinafter, an embodiment of the present invention will be described in detail with reference to the following Examples. However, it should be understood that these examples are provided for illustration only and are not to be in any way construed as limiting the embodiment.

Example 1: Confirmation of Effect of Composition Containing *Crepidiastrum denticulatum* Extract in Hepatic IRI Model Mouse 1. Preparation of *Crepidiastrum denticulatum* Extract In order to prepare a *Crepidiastrum denticulatum* (*C. denticulatum*) extract, an aerial part of *C. denticulatum* was purchased from Pyeongchang, Gangwon Province. After drying the purchased *C. denticulatum* in the shade, 600 g of the aerial part of *C. denticulatum* was added with 3 L of 70% ethanol and refluxed for 3 hours. The extract was dried under reduced pressure to obtain 80 g of a *C. denticulatum* ethanol extract.

2. Preparation of Hepatic IRI-Induced Mouse Model 10 week-old male C57BL/6 mice (body weight: 22 to 25 g) were purchased from DaeHanBioLink Co., Ltd, Eumseong, Korea. All experiments complied with the guidelines for the use and care of laboratory animals issued by the NIH (Publication No. 85-23, Rev. 1985) and were approved by the Ethics Committee of KIST (Gangneung, Korea). The mice were housed in standard laboratory conditions at a temperature of 22±2° C. and a relative humidity of 55%, and were fed with basic mouse feed and tap water.

Ischemia was performed by closing the portal vein with a microvascular forceps for 40 minutes. Reperfusion was performed by removing the portal vein occlusion clamp. Occlusion and reperfusion were identified as changes in the color of the liver, and were observed as a slight change in shade (paler shade) or a change to a slightly red color (blush). During the occurrence of ischemia-reperfusion, the animals were fed with warm saline water. A warm pad was used to maintain a constant body temperature of 37° C. A sham operation was performed in a similar fashion except for the portal vein clamp. Blood and liver tissue were collected 6 hours after reperfusion. The liver was harvested and frozen in a nitrogen solution and stored at −80° C. until further analysis. Blood samples were collected from the lower vena cava.

3. Comparing ALT, AST, and LDH Levels of *C. denticulatum* Extract-Administered Group, Sham Operation Group, and Control Group in Hepatic IRI-Induced Mouse Model The *C. denticulatum* extract was dissolved or suspended at 75 mg/kg in distilled water. Thirty mice were randomly divided into three groups of 10 mice each. For the sham group and IRI control group (IRI), only the solvent in which *C. denticulatum* did not dissolve was orally administered at a dose of 0.1 ml/20 g body weight (BW) once a day. In the experimental group, that is the *C. denticulatum*-treated group (CD+IRI), the *C. denticulatum* extract solution was orally administered intragastrically at a dose of 75 mg/kg body weight (BW) for 4 days before IRI.

The blood samples were collected from the inferior vena cava and centrifuged at a rate of 6000×g for 30 minutes at 4° C. to separate plasma or serum. FIG. 1 shows the preparation of mouse models and a schedule for drug administration and tissue resection. In FIGS. 1, 2A-2C, 3A, 3B, 4A-4C, 5, and 6A-6D, sham and IRI respectively represent "fake surgery" and ischemia-reperfusion injury, and CD represents an extract of *C. denticulatum* ethanol.

In order to confirm the effect of *C. denticulatum* extract on hepatic ischemia-reperfusion injury, levels of serum alanine transaminase (ALT), aspartate transaminase (AST), and lactate dehydrogenase (LDH), as liver function indexes, were measured. Values of ALT, AST, and LDH were measured by using a Kovas C702 analyzer (Roche, Germany) and data are expressed as average±standard deviation (SEM) (*$P<0.05$ for *C. denticulatum* extract (CD+IRI) vs. solvent-treated group (IRI), and Sham group (sham)). The results are shown in FIGS. 2A, 2B, and 2C. FIGS. 2A, 2B, and 2C show ALT, AST, and LDH levels, respectively in serum when the composition containing the *C. denticulatum* extract is administered to a hepatic IRI mouse model. As shown in FIGS. 2A, 2B, and 2C, serum ALT, AST, and LDH levels were significantly increased in the control group (IRI) compared to those of the sham group (sham), whereas serum ALT, AST, and LDH levels in the drug treatment group (CD+IRI) significantly decreased. This indicates that the *C. denticulatum* extract is effective in preventing or treating hepatic ischemia-reperfusion injury.

4. Measuring Change in Liver Tissue Caused by Administration of *C. Denticulatum* Extract in Hepatic IRI Mouse Model Immunohistochemistry was performed to examine the effect of the *C. denticulatum* extract on hepatic ischemia-reperfusion injury. The liver tissue obtained in Section 2 above was fixed with 10% formalin, frozen, dehydrated with 70 to 80% aqueous ethanol solution, infiltrated with paraffin, and sectioned to a thickness of 5 μm. Thereafter, hematoxylin-eosin (H&E) staining was performed on the tissue, and the tissue was observed with a microscope and photographed.

FIGS. 3A and 3B show the result of hematoxylin-eosin (H&E) staining of liver tissue when a composition containing *C. denticulatum* extract was administered to a hepatic IRI mouse model and histology score obtained from H&E staining, respectively. As shown in FIGS. 3A and 3B, normal hepatic lobule and hepatocyte morphology was observed in the stomach operation group (Sham), whereas distortion and extensive necrosis of the liver tissue were observed in the control group (IRI). In the *C. denticulatum* extract-treated group (IRI+CD), some necrosis and structural abnormality were observed in central veins, but liver damage was remarkably alleviated compared to the control (IRI).

In the case of acute hepatic necrosis, the degree of liver damage was graded as 0 to 4 as described below and graded. One whole deep coronal fragment was observed under a microscope and graded according to the extent of tubular necrosis based on renal tissue ratio. Higher scores indicate more serious damage. (4 points=maximum value, 0=normal level, 1=minimal cell necrosis, <30% relativity, 2=weak cell necrosis, ~60% relativity, 3=severe cell necrosis, >60% relativity, and 4=severe cell necrosis).

5. Confirmation of Changes in Liver Antioxidant Activity Caused by *C. Denticulatum* Extract in Hepatic IRI Mouse Model Regarding the effect of *C. denticulatum* extract on the prevention and treatment of hepatic IRI, in order to investigate effectiveness of antioxidant function of the *C. denticulatum* extract, a concentration of malondialdehyde (MDA), myeloperoxidase (MPO) activity, and an amount of glutathione in liver tissues were measured. In this measurement, the concentration of MDA, a lipid degradation product, was measured using a thiobarbituric acid reactive substance (TBARS) method as an indicator of the degree of lipid peroxidation. Liver tissues were lysed in cold lysis buffer (50 mM Tris-HCl, 150 mM NaCl, 1% NP-40, 0.5% sodium deoxycholic acid (DOC), 0.1% SDS, 1 mM PMSF, protease inhibitor, and phosphatase inhibitor) to prepare a tissue homogenate, and then the supernatant was separated by centrifugation at 13,000 rpm for 10 minutes. 200 µl of the supernatant and 600 µl of TBA reagent were mixed and heated at 95° C. for 1 hour. The mixture was cooled on ice for 10 minutes, and then the mixed solution was taken using a 0.22 µm filter. An absorbance of the supernatant thus obtained was measured at 532 nm using a spectrophotometer.

To determine a glutathione content, 5% 5-sulfosalicylic acid, which was 5 times the number of liver tissues in terms of their amounts, was added to the liver tissues to prepare a tissue homogenate. After centrifugation at 4° C. for 5 minutes, 700 µl of 0.248 mg/ml NADPH, 100 µl of 6 mM DTNB, and 180 µl of purified water were mixed, and the temperature was adjusted to 30° C. in advance. The reaction was started by adding 20 µl of the supernatant and 10 µl of 266 unit/ml GSSG reductase. A slope was obtained by observing the change of absorbance for 3 minutes at intervals of 10 seconds using an ELISA reader, and the content was calculated by comparing the slope with a 100 mM glutathione standard solution.

In addition, 200 µl of soluble buffer was homogenized in 100 mg of liver tissue, and then the resultant was centrifuged at 13,000 rpm at 4° C. for 15 minutes to obtain a supernatant, from which MPO activity was measured using a mouse MPO assay ELISA kit (Hbt HK210, USA). In particular, 100 µl of the supernatant was added to a 96-well plate and allowed to react at room temperature for 1 hour. Once the reaction was completed, the plate was emptied, and the kit was washed with a washing buffer. Then, 100 µl of a streptavidin-peroxidase conjugate was added, and the reaction was allowed to proceed at room temperature for 1 hour. After completion of the reaction, the plate was emptied and washed with a washing buffer solution. Then, 100 µl of TMB substrate solution was added thereto, and the plate was wrapped with aluminum foil and allowed to react at room temperature for 30 minutes. Thereafter, 100 µl of a stop solution of the kit was added to the reaction to stop the reaction, and an absorbance at UV 450 nm was measured using an ELISA reader.

FIGS. 4A, 4B, and 4C show the results of measurement of MDA, MPO, and glutathione levels, respectively in the liver when a composition containing *C. denticulatum* extract was administered to a hepatic IRI mouse model. As shown in FIGS. 4A, 4B, and 4C, in the liver ischemia-reperfusion control group (IRI), MDA concentration and MPO activity were increased due to ischemia-reperfusion injury, and glutathione content was significantly decreased compared to the sham operation group (Sham). However, in the *C. denticulatum* extract-treated group (CD+IRI), the MDA concentration, MPO activity, and glutathione content were changed to the same levels as those of the sham group (Sham), and thus it was confirmed that the antioxidant activity of the *C. denticulatum* extract is highly associated with the efficacy of prevention or treatment of hepatic ischemia-reperfusion injury.

6. Analysis of Change in Protein Expression Caused by *C. denticulatum* Extract in Hepatic IRI Mouse Model To investigate the mechanism of the protective effect of the *C. denticulatum* extract on hepatic IRI, protein expression related to oxidation, inflammation, or apoptosis was examined by Western blotting.

Liver tissues were mashed in an ice buffer including 1 M Tris-HCl buffer, pH 7.5 protease inhibitor, 25 mM sodium fluoride, 10 mM sodium orthovanadate, 0.5 mol/L ethylenediaminetetraacetic acid (EDTA), and a surfactant (1% Triton X-100; GenDEPOT, Barker, Tex., USA), and then centrifuged at 14,000 rpm for 20 minutes. Protein concentrations were measured using a Bradford protein assay (Bio-Rad, Hercules, USA). 20 µg of protein extract was separated from 10%, 15% sodium dodecyl sulfate polyacrylamide gel (SDS-PAGE; Bio-Rad, USA) and moved to nitrocellulose membranes (Bio-Rad, Hercules, USA). The membranes were blocked for 120 min in 5% skimmed milk in Tris-buffered saline and Tween 20 (TBST) buffer (10 mM Tris-base, 100 mM NaCl, and 0.1% Tween-20, pH 8.0), and were washed three times with TBS/T.

Next, primary antibodies corresponding to HSP70, Bcl-2-associated X protein (Bax), caspase 3, high mobility group box-1 (HMGB1), phosphorylated-IκBα (p-IκBα), nuclear factor-kappa B p65 (NF-κBp65), toll-like receptor 2 (TLR2), toll-like receptor 4 (TLR4), and inducible nitric oxide synthase (iNOS) were reacted overnight at 4° C. HRP-conjugated secondary antibodies, of which horseradish peroxidase (HRP) was attached to primary antibodies attached to the membrane, were confirmed using an EZ-Capture ST imaging system (Atto, Japan), and blot images were collected for quantitative analysis. The results are shown in FIGS. 5, 6A-6D, 7A-7C, 8A, and 8B.

FIG. 5 shows the Western blot results of biological factors involved in the effect of *C. denticulatum* extract on hepatic IRI.

FIGS. 6A-6D are graphs that show the Western blot results of major factors involved in the effect of *C. denticulatum* extract on hepatic IRI. FIG. 6A Heat shock protein 70 (HSP70), FIG. 6B inducible nitric oxide synthase (iNOS), FIG. 6C toll-like receptor 4 (TLR4), and FIG. 6D toll-like receptor 2 (TLR2).

FIGS. 7A, 7B, and 7C are graphs that show the Western blot results of major factors involved in the effect of *C. denticulatum* extract on hepatic IRI. FIG. 7A Nuclear factor-kappa B p65 (NF-κBp65), FIG. 7B phosphorylated-IκBα (p-IκBα), and FIG. 7C high mobility group box-1 (HMGB1).

FIGS. 8A and 8B are graphs that show the Western blot results of major factors involved in the effect of *C. denticulatum* extract on hepatic IRI. FIG. 8A Caspase 3, and FIG. 8B Bax (Bcl-2-associated X protein).

As shown in FIGS. 5, 6A-6D, 7A-7C, 8A, and 8B, in the hepatic IRI control group, expression of proteins related to inflammation such as iNOS, TLR4, TLR2, NF-κBp65, and HSP70 were increased, and the *C. denticulatum* extract was confirmed to suppress expression of inflammatory response factors caused by surgery or ischemia-reperfusion injury. On the other hand, the *C. denticulatum* hepatic ischemia-reperfusion injury protection effect was not related to inflammatory factors of HMGB1 and p-IκBα (FIGS. 5 and 7A-7C) or apoptosis factors such as caspase3 and Bax (FIGS. 5, 8A, and 8B).

Example 2: Confirmation of Effect of Composition Containing *C. denticulatum* Extract in Renal IRI Model Mouse 1. Preparation of Renal IRI-Induced Mouse Model Purchasing and feeding of mice in which renal IRI was induced were performed under the same conditions as in Section 2 of Example 1. Ischemia was performed by closing both renal pedicles with a microvascular forceps for 30 minutes. Reperfusion was performed by removing the renal pedicle occlusion clamp. Occlusion and reperfusion were identified as changes in the color of the kidney and were observed as a change to dark purple or a slightly red color (blush). During the induction of ischemia-reperfusion injury, the animals were fed with warm saline water. A warm pad was used to maintain a constant body temperature of 37° C. A sham operation was performed in a similar fashion without using the renal pedicle clamp. Blood and kidney tissue were collected 48 hours after reperfusion. Both the kidneys were harvested and frozen in a nitrogen solution and stored at −80° C. until further analysis. Blood samples were collected from the lower vena cava.

2. Comparing *C. denticulatum* Extract-Administered Group, Sham Operation Group, and Control Group in Renal IRI-Induced Mouse Model The *C. denticulatum* extract was dissolved or suspended at 75 mg/kg in tertiary distilled water. Thirty mice were randomly divided into three groups of 10 mice each. For the sham group and the IRI group control (IRI), only the solvent in which *C. denticulatum* was not dissolved was orally administered at a dose of 0.1 ml/20 g body weight (BW) once a day. In the experimental group, that is the *C. denticulatum*-treated group (CD+IRI), the *C. denticulatum* extract solution was orally administered intragastrically at a dose of 75 mg/kg body weight (BW) once a day until day 2 after the treatment from 4 days before IRI.

Blood samples were collected from the inferior vena cava. Blood urea nitrogen (BUN) and serum creatinine levels were measured with a Kobas C702 analyzer (Roche, Germany). The results of each experiment were expressed as average±standard deviation (SEM) (*P<0.05 *C. denticulatum* extract (CD+IRI) vs. solvent treatment group (IRI), sham operation group (sham)).

The results are shown in FIGS. 9A and 9B. FIGS. 9A and 9B show blood BUN levels and serum creatinine levels, respectively when a composition containing *C. denticulatum* extract is administered to a renal IRI mouse model. As shown in FIGS. 9A and 9B, IRI in the solvent-treated mice (IRI group) caused renal dysfunction. Two days after IRI, BUN and serum creatinine levels were significantly elevated. On the other hand, BUN and creatinine levels were significantly decreased in the drug-administered group (CD+IRI). This indicates that the composition containing *C. denticulatum* extract has an effect of preventing or decreasing ischemia-reperfusion renal damage.

As described above, according to one embodiment, a pharmaceutical composition for preventing or treating ischemia-reperfusion injury in a subject may be used to prevent or treat ischemia-reperfusion injury in a subject.

According to another embodiment, a food composition for preventing or treating ischemia-reperfusion injury in a subject may be used as food for preventing or treating ischemia-reperfusion injury in a subject.

According to another embodiment, when a method of preventing or treating ischemia-reperfusion injury in a subject is used, ischemia-reperfusion injury of a subject may be effectively prevented or treated.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A method of preventing or treating ischemia-reperfusion injury in a subject, the method comprising administering a pharmaceutical composition to the subject, wherein the subject is a mammal, wherein the pharmaceutical composition comprises a *Crepidiastrum denticulatum* (CD) extract as an active ingredient for preventing or treating ischemia-reperfusion injury in the subject.

2. The method of claim 1, wherein the extract is extracted by using an extraction solvent comprising water, a C1-C6 alcohol, or a mixture thereof.

3. The method of claim 2, wherein the alcohol is methanol, ethanol, propanol, isopropanol, butanol, or a mixture thereof.

4. The method of claim 1, wherein the ischemia is artificially induced.

5. The method of claim 4, wherein the artificially induced ischemia comprises artificially decreasing blood flow in a blood vessel.

6. The method of claim 5, wherein the artificial decreasing of the blood flow comprises clogging or blocking the blood vessel.

7. The method of claim 5, wherein the artificial decreasing of the blood flow is performed during surgery.

8. The method of claim 7, wherein the surgery comprises transplantation surgery, tissue resection, aneurysm repair surgery, or endarterectomy.

9. The method of claim 8, wherein the transplantation surgery comprises transplantation of heart, liver, kidney, lung, pancreas, stomach, small intestine, or large intestine.

10. The method of claim 8, wherein the tissue resection comprises resection of liver, kidney, lung, stomach, small intestine, or large intestine.

11. The method of claim 1, wherein the ischemia is caused by an ischemic disorder.

12. The method of claim 1, wherein the reperfusion is performed by artificial reperfusion.

13. The method of claim 12, wherein the artificial reperfusion comprises artificially increasing blood flow in a blood vessel.

14. The method of claim 13, wherein the artificial increasing of the blood flow comprises opening a clogged or closed blood vessel or connecting severed blood vessels.

15. The method of claim 1, wherein at least one of the ischemia and the reperfusion is artificially induced.

16. The method of claim 1, wherein the ischemia continues for about 10 minutes to about 60 minutes.

17. The method of claim 1, wherein the ischemia-reperfusion injury is injury to liver, kidney, heart, lung, small intestine, large intestine, or pancreas.

18. The method of claim 1, wherein administration of the composition is performed before, at the same time, or after the ischemia-reperfusion injury occurs.

19. The method of claim 7, wherein administration of the composition is performed before, at the same time, or after the surgery.

\* \* \* \* \*